United States Patent [19]

Iritani et al.

[11] Patent Number: 5,475,140

[45] Date of Patent: Dec. 12, 1995

[54] PROCESS FOR PRODUCING N,N-DISUBSTITUTED P-PHENYLENEDIAMINE DERIVATIVE SULFATE

[75] Inventors: Takehiko Iritani; Ryohiko Kinoshita; Yoshiki Kametani, all of Kawagoe, Japan

[73] Assignee: Wako Pure Chemical Industries, Ltd., Osaka, Japan

[21] Appl. No.: 229,943

[22] Filed: Apr. 19, 1994

[30] Foreign Application Priority Data

Apr. 21, 1993 [JP] Japan .................................. 5-117967

[51] Int. Cl.$^6$ ................................................ C07C 209/38
[52] U.S. Cl. ............................ 564/418; 564/410; 564/414
[58] Field of Search .................................... 564/410, 418, 564/419, 416, 423, 414

[56] References Cited

U.S. PATENT DOCUMENTS 3,624,259  11/1971  Galantay ............................. 260/479 R
4,474,987  10/1984  Wollemann et al. ................... 564/420
4,479,008  10/1984  Batorewicz et al. ................... 564/433

FOREIGN PATENT DOCUMENTS 280837   5/1952  Switzerland .
2065657  7/1981  United Kingdom .

OTHER PUBLICATIONS

Berichte, 8, 616–622 (1875).

*Primary Examiner*—Glennon H. Hollrah
*Assistant Examiner*—Brian M. Burn
*Attorney, Agent, or Firm*—Armstrong, Westerman, Hattori, McLeland & Naughton

[57] ABSTRACT

4-Amino-3-methyl-N-ethyl-N-(β-hydroxyethyl)-aniline sulfate which is used particularly as a developer for color photography can be easily produced in high yield and high quality by nitrosating N-ethyl-N-(β-hydroxyethyl)-m-toluidine by use of an alkyl nitrite in a homogeneous alcohol solution containing sulfuric acid in an amount of about 0.5 to about 1 mole per mole of N-ethyl-N-(β-hydroxyethyl)-m-toluidine, and then reducing the nitrosation product in an aqueous alcohol solution after or without isolation of the nitrosation product.

10 Claims, No Drawings

PROCESS FOR PRODUCING N,N-DISUBSTITUTED P-PHENYLENEDIAMINE DERIVATIVE SULFATE

BACKGROUND OF THE INVENTION

This invention relates to a process for producing 4-amino-3-methyl-N-ethyl-N-(β-hydroxyethyl)-aniline sulfate which is used not only as an intermediate of various azo dyes, medicines, agrochemicals, etc. but also particularly as a developer for color photography.

As processes for synthesizing a p-phenylenediamine derivative from an aniline derivative through a corresponding nitrosation product of the aniline derivative, there are known, for example, a process of reacting sodium nitrite and hydrochloric acid with an aniline derivative in water as solvent to obtain a p-nitrosoaniline derivative, followed by reducing this derivative [for example, J. Am. Chem. Soc., 73, 3100 (1951)], and a process of reacting an alkyl nitrite with an aniline derivative in an aqueous acid suspension, followed by reducing the thus obtained nitroso compound without isolation [U.S. Pat. No. 4,474,987 (Japanese Patent Examined Publication No. 63-53981)]. The former process, however, requires unavoidably a troublesome purification procedure for removal of various by-products because of side reactions during the nitrosation, and gives an insufficient yield. On the other hand, the latter process is superior to the former process in the quality and yield of the product but has various defects, for example, in that the nitrosation reaction by use of the alkyl nitrite is carried out in a heterogeneous system because alkyl nitrites are almost insoluble in water which is used as a solvent, and a large portion of the water used as solvent should be distilled off, because a finally desired acid salt of the p-phenylenediamine derivative is highly water-soluble, resulting in a low work-efficiency. Further, since water alone is used as a solvent in the catalytic reduction of nitrosation product, hydrogen absorption efficiency is poor and a relatively long time is required for the catalytic reduction.

As described above, the conventional processes comprising nitrosation of an aniline derivative at the p-position followed by reduction involve, for example, the following problems: i) a troublesome purification procedure is necessary because of side reactions occurred during the nitrosation, ii) the nitrosation reaction does not proceeds smoothly owing to a heterogeneous reaction system, iii) a long time is required for removing water used as a solvent. All of these problems cause a cost-increase when the processes are put to practical use. Therefore, a more practical production process free from the above problems is desired.

SUMMARY OF THE INVENTION

The present inventors earnestly investigated to find a process for obtaining 4-amino-3-methyl-N-ethyl-N-(β-hydroxyethyl)aniline sulfate with industrial advantages, and found an excellent process capable of solving the above problems.

That is, this invention provides a process for producing 4-amino-3-methyl-N-ethyl-N-(β-hydroxyethyl)-aniline sulfate which comprises nitrosating N-ethyl-N-(β-hydroxyethyl)-m-toluidine by use of an alkyl nitrite in a homogeneous alcohol solution containing sulfuric acid in an amount of about 0.5 to about 1 mole per mole of N-ethyl-N-(β-hydroxyethyl)-m-toluidine, and then reducing the nitrosation product in an aqueous alcohol solution after or without isolation of the nitrosation product.

DESCRIPTION OF THE PREFERRED EMBODIMENTS

As N-ethyl-N-(β-hydroxyethyl)-m-toluidine used as a starting material in this invention, a commercially available material may be used as it is or after being properly purified if necessary. Since this compound can be synthesized by a known method, for example, a method of reacting N-ethyl-m-toluidine with ethylene oxide, ethylene chlorohydrin or the like. N-ethyl-N-(β-hydroxyethyl)-m-toluidine synthesized by such a method may be used.

As the alkyl nitrite used as a nitrosating agent, alkyl nitrites having preferably 3 to 5 carbon atoms, such as isopropyl nitrite, n-propyl nitrite, isobutyl nitrite, n-butyl nitrite, isoamyl nitrite, etc. are usually preferable, but the alkyl nitrite is not limited to them. Among these alkyl nitrites, the use of isopropyl nitrite is more preferable. These alkyl nitrites can be easily synthesized separately by a known method, for example, a method of reacting an alkali metal nitrite with an alcohol in the presence of an acid such as hydrochloric acid or sulfuric acid. An alkyl nitrite obtained by such a method may be used.

As the alcohol used as an aqueous alcohol for the nitrosation of N-ethyl-N-(β-hydroxyethyl)-m-toluidine, any alcohol may be used without any trouble so long as it is easily miscible with water. Examples of the alcohol are ethanol, isopropanol, n-propanol, isobutanol, n-butanol, isoamyl alcohol, etc. Among them, isopropanol is more preferable. Employment of an alcohol having the same alkyl group as that of the alkyl nitrite used is preferable because it is advantageous in view of the recovery of the solvent. For example, when isopropyl nitrite is used as a nitrosating agent, the use of isopropanol is preferable. The alcohol concentration is optional in the range of 30 to 90% by volume (v/v). But, when the alcohol concentration is low, the solubility of the alkyl nitrite is lowered and the reaction rate of the subsequent reduction tends to be decreased. When the alcohol concentration is high, sulfate of the nitrosation product formed by sulfuric acid added at the time of the nitrosation separates out as oil or paste in some cases. When the sulfate of the nitrosation product is isolated after nitrosation step, the alcohol concentration is preferably 80 to 90% v/v in the nitrosation step, and preferably 80–95% v/v in the reduction step. When the sulfate of the nitrosation product is not isolated and subjected to the reduction step as it is, the alcohol concentration is preferably 30 to 70% v/v. Although the volume of the solvent used is not critical, it is preferably a volume corresponding to 3 to 5 times the weight of N-ethyl-N-(β-hydroxyethyl)-m-toluidine because too large a volume or too small a volume is disadvantageous as follows. When the volume of the solvent used is too large, the product-yield is not sufficient. When the volume of the solvent used is too small, stirring of the reaction mixture becomes difficult.

The nitrosation reaction by use of the alkyl nitrite proceeds smoothly by virtue of the presence of sulfuric acid. The amount of sulfuric acid added is preferably about 0.5 to about 1 mole, more preferably about 0.5 mole to 0.75 mole, most preferably about 0.5 to 0.6 mole per mole of N-ethyl-N-(β-hydroxyethyl)-m-toluidine. When the amount of sulfuric acid is too small, the reaction rate is decreased. When the amount of sulfuric acid is too large, a troublesome after-treatment is required. Therefore, both of such amounts are not desirable.

The nitrosation reaction is carried out usually at −20° C. to +20° C. preferably −5° C. to +5° C. Although the reaction time is dependent on the kind of the alkyl nitrite, 2 to 5 hours is usually sufficient. The amount of the alkyl nitrite is a little larger than the theoretical amount and is preferably about 1.1 moles. In this case, the excess alkyl nitrite present at the time of completion of the reaction need not be removed because it does not cause undesirable side reactions.

N-ethyl-N-(β-hydroxyethyl)-3-methyl-4-nitrosoaniline sulfate obtained by the nitrosation method according to this invention can be used in the subsequent reduction step after isolation or in the form of a reaction mixture. As the reduction method of N-ethyl-N-(β-hydroxyethyl)-3-methyl-4-nitrosoaniline sulfate according to this invention, catalytic hydrogenation (catalytic reduction) is the most preferable. In addition to this method, reduction methods using a metal such as iron powder or zinc powder can also be applicable.

The reduction method according to this invention is explained below by taking the case of catalytic hydrogenation. Hydrogenation reaction is carried out while adding the sulfate of the nitrosation product, in the presence of a suitable catalyst (e.g. palladium, palladium-carbon, platinum oxide or platinum-carbon) at 20°–50° C. and a hydrogen pressure of atmospheric pressure to 10 kg/cm$^2$, preferably at 35°–45° C. and a hydrogen pressure of 3–5 kg/cm$^2$. When the nitrosoaniline sulfate is isolated after nitrosation step, the hydrogenation can preferably be carried out in a solvent used for crystallizing the final desired product [e.g. ethanol or aqueous ethanol (preferably 80–95% v/v of ethanol)]. When the nitrosoaniline sulfate is in the form of a reaction mixture, the hydrogenation is carried out in the same aqueous alcohol as used for the nitrosation reaction, while adjusting the concentration of alcohol, if necessary. Although the reaction time varies a little depending on the reaction temperature, the kind of the catalyst, hydrogen pressure, etc., 1 to 6 hours is usually sufficient.

After completion of the reaction, the catalyst is filtered off. If necessary, the resulting filtrate (reaction mixture) is concentrated to remove the reaction solvent for reaction (this procedure is not always necessary when the nitrosoaniline sulfate is reduced after isolation as mentioned above). The residue is redissolved in a solvent for recrystallization of the final desired compound, such as ethanol or aqueous ethanol (preferably 80–95% v/v of ethanol), and concentrated sulfuric acid is, if necessary, properly added so as to form the desired sulfate, followed by crystallization, collection of crystals by filtration, and drying. Particularly, when about 0.5 mole to about 0.75 mole of sulfuric acid per mole of N-ethyl-N-(β-hydroxyethyl)-m-toluidine is added to the nitrosation reaction, it is preferable to add the insufficient amount of sulfuric acid, preferably in the form of concentrated sulfuric acid, for producing 4-amino- 3-methyl-N-ethyl-N-(β-hydroxyethyl)aniline monosulfate at the time of crystallization step after the reduction of nitrosation product. Thus, 4-amino-3-methyl-N-ethyl-N-(β-hydroxyethyl)aniline sulfate can be obtained in a high yield and high quality.

This invention is illustrated below in further detail with reference to Examples, which are not by way of limitation but by way of illustration.

Example 1

(1) Synthesis of N-ethyl-N-(β-hydroxyethyl)-3-methyl-4-nitrosoaniline.1/2 sulfate With 89.6 g (0.5 mole) of N-ethyl-N-(β-hydroxyethyl)-m-toluidine was mixed 270 ml of 80% v/v isopropanol, and 24.5 g (0.25 mole) of sulfuric acid was added with cooling and stirring at 10° C. or lower. After 49.0 g (0.55 mole) of isopropyl nitrite was added dropwise at 10° C. or lower, the reaction was carried out at 2° C. or lower for another 4 hours. After completion of the reaction, the crystals precipitated were collected by filtration to obtain 119.7 g of N-ethyl-N-(β-hydroxyethyl)-3-methyl-4-nitrosoaniline.1/2 sulfate as yellow-green powder. Yield: 93.0%. Decomposition point: 74° C.

The purity of N-ethyl-N-(β-hydroxyethyl)- 3-methyl-4-nitrosoaniline.1/2 sulfate was as high as 99.7% as measured by high pressure liquid chromatography (HPLC). Therefore, the product was used in the subsequent step as it was.

$^1$HNMR δ ppm (DMSO-d$_6$): 1.25 (3H, t, CH$_3$), 2.68 (3H, s, CH$_3$), 3.72 (2H, t, CH$_2$), 3.80–3.88 (4H, m, CH$_2$×2), 5.10–6.40 (2H, b, OH×2), 7.07 (1H, d, arom-H), 7.09 (1H, s, arom-H), 7.22 (1H, d, arom-H) IR ν cm$^{-1}$ (KBr disk): 1420 (—NO)

(2) Synthesis of 4-amino-3-methyl-N-ethyl-N-(β-hydroxyethyl)aniline sulfate

In 206 ml of 90% v/v ethanol was suspended 2.9 g (0.4 mole) of the N-ethyl-N-(β-hydroxyethyl)- 3-methyl-4-nitrosoaniline.1/2 sulfate obtained in (1) above, and hydrogenation was carried out at 40°–45° C. and at a hydrogen pressure of 9–10 kg/cm$^2$ while adding the suspension to 103 ml of 90% v/v ethanol containing 5.2 g of 5% palladium-carbon over a period of 4 hours. After completion of the reaction, the catalyst was filtered off and 19.6 g (0.2 mole) of sulfuric acid was added to the filtrate at 45°–50° C. Then, the resulting mixture was cooled for 2 hours to carry out crystallization, and the crystals thus formed were collected by filtration at 2° C., washed with 100 ml of cold ethanol, and then dried to obtain 107.4 g of 4-amino- 3-methyl-N-ethyl-N-(β-hydroxyethyl)aniline sulfate as white powder. Yield: 91.8%. Melting point: 153.9° C. The purity of 4-amino-3-methyl-N-ethyl-N-(β-hydroxyethyl)aniline sulfate was 100% as measured by HPLC, namely, no impurity was detected at all. (Yield from N-ethyl-N-(β-hydroxyethyl)-m-toluidine: 85.4% ).

$^1$HNMR δ ppm (D$_2$O): 1.14 (3H, t, CH$_3$), 2.45 (3H, s, CH$_3$), 3.70–3.79 (6H, m, CH$_2$×3), 7.55 (3H, d, arom-H) IR ν cm$^{-1}$ (KBr disk): 3280, 2890, 1580, 1510

Example 2

With 89.6 g (0.5 mole) of N-ethyl-N-(β -hydroxyethyl)-m-toluidine was mixed 270 ml of 50% v/v isopropanol, and 24.5 g (0.25 mole) of sulfuric acid was added with cooling and stirring at 10° C. or lower. After 49.0 g (0.55 mole) of isopropyl nitrite was added dropwise at 10° C. or lower, the reaction was carried out at 2°–5° C. for another 3 hours. After completion of the reaction, hydrogenation was carried out at 40°–45° C. and at a hydrogen pressure of 3–5 kg/cm$^2$ while adding the nitrosation reaction mixture to 270 ml of 50% v/v isopropanol containing 6.5 g of 5% palladium-carbon over a period of 2 hours. After completion of the hydrogenation, the catalyst was filtered off and the filtrate was concentrated to dryness to remove the solvent. The residue was dissolved in 270 ml of 90% v/v ethanol with heating and 24.5 g (0.25 mole) of sulfuric acid was added at 45°–50° C. Then, the resulting mixture was cooled for 2 hours to carry out crystallization, and the crystals thus formed were collected by filtration at 3° C., washed with 100 ml of cold ethanol, and then dried to obtain 133.3 g of 4-amino-3-methyl-N-ethyl-N-(β-hydroxyethyl)aniline sulfate as white powder. Yield: 91.2%. Melting point: 154.6° C. The purity of 4-amino-3-methyl-N-ethyl-N-(β-hydroxyethyl)aniline sulfate was 100% as measured by HPLC, namely, no impurity was detected at all.

$^1$HNMR δ ppm (D$_2$O): 1.14 (3H, t, CH$_3$), 2.45 (3H, s, CH$_3$), 3.70–3.79 (6H, m, CH$_2$×3), 7.55 (3H, d, arom-H) IR ν cm$^{-1}$ (KBr disk): 3280, 2890, 1580, 1510

Example 3

With 89.6 g (0.5 mole) of N-ethyl-N-(β-hydroxyethyl)-m-toluidine was mixed 270 ml of 30% v/v isopropanol, and 24.5 g (0.25 mole) of sulfuric acid was added with cooling and stirring at 10° C. or lower. After 49.0 g (0.55 mole) of isopropyl nitrite was added dropwise at 10° C. or lower, the reaction was carried out at 2°–5° C. for another 2 hours. After completion of the reaction, hydrogenation was carried out at 40°–45° C. and at a hydrogen pressure of 8–10 kg/cm$^2$ while adding the nitrosation reaction mixture to 270 ml of 30% v/v isopropanol containing 6.5 g of 5% palladium-carbon over a period of 3 hours. After completion of the hydrogenation, the catalyst was filtered off and the filtrate was concentrated to dryness to remove the solvent. The residue was dissolved in 270 ml of 90% v/v ethanol with heating and 24.5 g (0.25 mole) of sulfuric acid was added at 45°–50° C. Then, the resulting mixture was cooled for 2 hours to carry out crystallization, and the crystals thus formed were collected by filtration at 3° C., washed with 100 ml of cold ethanol, and then dried to obtain 133.0 g of 4-amino-3-methyl-N-ethyl-N-(β-hydroxyethyl)aniline sulfate as white powder. Yield: 91.0%. Melting point: 154.6° C. The purity of 4-amino-3-methyl-N-ethyl-N-(β-hydroxyethyl)aniline sulfate was 100% as measured by HPLC, namely, no impurity was detected at all.

Example 4

With 89.6 g (0.5 mole) of N-ethyl-N-(β-hydroxyethyl)-m-toluidine was mixed 270 ml of 70% v/v isopropanol, and 24.5 g (0.25 mole) of sulfuric acid was added with cooling and stirring at 10° C. or lower. After 49.0 g (0.55 mole) of isopropyl nitrite was added dropwise at 10° C. or lower, the reaction was carried out at 2°–5° C. for another 4 hours. After completion of the reaction, hydrogenation was carried out at 40°–45° C. and at a hydrogen pressure of 3–5 kg/cm$^2$ while adding the nitrosation reaction mixture to 270 ml of 70% v/v isopropanol containing 6.5 g of 5% palladium-carbon over a period of 1.5 hours. After completion of the hydrogenation reaction, the catalyst was filtered off and the filtrate was concentrated to dryness to remove the solvent. The residue was dissolved in 270 ml of 90% v/v ethanol with heating and 24.5 g (0.25 mole) of sulfuric acid was added at 45°–50° C. Then, the resulting mixture was cooled for 2 hours to carry out crystallization, and the crystals thus formed were collected by filtration at 3° C., washed with 100 ml of cold ethanol, and then dried to obtain 132.7 g of 4-amino- 3-methyl-N-ethyl-N-(β-hydroxyethyl)aniline sulfate as white powder. Yield: 90.8%. Melting point: 154.6° C. The purity of 4 -amino-3-methyl-N-ethyl-N-(β-hydroxyethyl)aniline sulfate was 100% as measured by HPLC, namely, no impurity was detected at all.

Comparative Example 1

105.2 Grams of 4-amino-3-methyl-N-ethyl-N-(β-hydroxyethyl)aniline sulfate was obtained as brownish-white powder by carrying out the reactions and the after-treatment in exactly the same manner as described in Example 2, except that as a solvent for nitrosation and reduction, water was used in place of 50% v/v isopropanol. Yield: 72.0%.

Comparative Example 2

129.6 Grams of 4-amino-3-methyl-N-ethyl-N-(β-hydroxyethyl)aniline sulfate was obtained as white powder by carrying out the reactions and the after-treatment in exactly the same manner as described in Example 2, except that as a solvent for nitrosation and reduction, water was used in place of 50% v/v isopropanol, and that the nitrosation reaction mixture was added to the reduction system over a period of 6 hours. Yield: 88.7%.

As is clear from the results of Comparative Examples 1 and 2, when water is used as a solvent for nitrosation and reduction, the reduction requires a time longer than that required when 50% v/v isopropanol is used as the solvent.

Comparative Example 3

When the nitrosation reaction was carried out in the same manner as in Example 2 except for using isopropanol as a solvent in place of 50% v/v isopropanol, the product separated out as paste in the reaction mixture, so that the subsequent procedure could not be carried out.

As mentioned above, according to the present invention, high quality 4-amino-3-methyl-N-ethyl-N-(β-hydroxyethyl)aniline sulfate, which is used particularly as a developer for color photography, can be produced in high yield by a simple process. Therefore, this invention contributes greatly to the art.

What is claimed is:

1. A process for producing 4-amino-3 -methyl-N-ethyl-N-(β-hydroxyethyl)aniline sulfate which comprises nitrosating N-ethyl-N-(β-hydroxyethyl)-m-toluidine with an alkyl nitrite in an aqueous alcohol solution containing 30–90% by volume of the alcohol and about 0.5 to about 1 mole of sulfuric acid per mole of the N-ethyl-N-(β-hydroxyethyl)-m-toluidine to form N-ethyl-N-(β-hydroxyethyl)-3-methyl-4-nitrosoaniline sulfate, and catalytically hydrogenating the N-ethyl-N-(β-hydroxyethyl)-3-methyl-4-nitrosoaniline sulfate.

2. A process according to claim 1, wherein the N-ethyl-N-(β-hydroxyethyl)-3-methyl-4-nitrosoaniline sulfate is not isolated prior to catalytic hydrogenation.

3. A process according to claim 2, wherein the alkyl moiety of the alkyl nitrite has 3 to 5 carbon atoms.

4. A process according to claim 3, wherein the alkyl nitrite is isopropyl nitrite.

5. A process according to claim 1, wherein the aqueous alcohol solution contains about 0.5 mole to 0.75 mole per mole sulfuric acid of N-ethyl-N-(β-hydroxyethyl)-m-toluidine.

6. A process according to claim 5, which comprises the additional step of adding sulfuric acid to convert any methyl-N-ethyl-N-(β-hydroxyethyl)aniline formed during catalytic hydrogenation step to methyl-N-ethyl-N-(β-hydroxyethyl)aniline sulfate.

7. A process according to claim 1, wherein the N-ethyl-N-(β-hydroxyethyl)-3-methyl-4-nitrosoaniline sulfate is isolated prior to catalytic hydrogenation.

8. A process according to claim 7, wherein the N-ethyl-N-(δ-hydroxyethyl)-m-toluidine is nitrosated in an aqueous alcohol solution containing 80–90% by volume of the alcohol, and the N-ethyl-N-(β-hydroxyethyl)-3-methyl-4-nitrosoaniline is catalytically hydrogenated in an aqueous alcohol solution containing 80–95% by volume of the alcohol.

9. A process according to claim 8, wherein the alcohol is isopropanol, and the alkyl nitrite is isopropyl nitrite.

10. A process according to claim 9, which comprises the additional step of adding sulfuric acid to convert any methyl-N-ethyl-N-(β-hydroxyethyl)aniline formed during catalytic hydrogenation step to methyl-N-ethyl-N-(β-hydroxyethyl)aniline sulfate.

\* \* \* \* \*